US008753623B2

(12) United States Patent
He et al.

(10) Patent No.: US 8,753,623 B2
(45) Date of Patent: *Jun. 17, 2014

(54) INFLUENZA VACCINE

(76) Inventors: Runtao He, Winnipeg (CA); Xuguang Li, Ottawa (CA); Gary Van Domselaar, Winnipeg (CA)

( * ) Notice: Subject to any disclaimer, the term of this patent is extended or adjusted under 35 U.S.C. 154(b) by 80 days.

This patent is subject to a terminal disclaimer.

(21) Appl. No.: 13/266,801

(22) PCT Filed: Apr. 29, 2010

(86) PCT No.: PCT/CA2010/000623
§ 371 (c)(1),
(2), (4) Date: Dec. 1, 2011

(87) PCT Pub. No.: WO2010/124373
PCT Pub. Date: Nov. 4, 2010

(65) Prior Publication Data
US 2012/0070455 A1 Mar. 22, 2012

Related U.S. Application Data

(60) Provisional application No. 61/173,842, filed on Apr. 29, 2009.

(51) Int. Cl.
*A61K 39/145* (2006.01)
*G01K 7/08* (2006.01)
*C12Q 1/70* (2006.01)
C07K 16/10 (2006.01)
C07K 17/06 (2006.01)
G01N 33/569 (2006.01)

(52) U.S. Cl.
USPC .... 424/93.1; 530/327; 530/387.9; 530/389.4; 530/403; 530/405; 424/186.1; 435/5; 435/7.1

(58) Field of Classification Search
None
See application file for complete search history.

(56) References Cited

U.S. PATENT DOCUMENTS 5,916,803 A * 6/1999 Sedlacek et al. ............ 435/320.1

FOREIGN PATENT DOCUMENTS

| WO | 2004080403 | | 9/2004 |
|---|---|---|---|
| WO | WO2004086403 | * | 9/2004 |
| WO | 2008124646 | | 10/2008 |

OTHER PUBLICATIONS

Database WPI, Week 200718, Thomson Scientific, London, GB; An 2007-178722, Oct. 5, 2006.
Nayana Prabhu et al: "Monoclonal Antibodies against the Fusion Peptide of Hemagglutinin Protect Mice from Lethal Influenza A Virus H5N1 Infection", Journal of Virology, the American Society for Microbiology, US, vol. 83, No. 6, Dec. 24, 2008, pp. 2553-2562.
Vareekova e et al: "Inhibition of fusion activity of influenza A haemagglutinin mediated by HA2-specific monoclonal antibodies", Archives of Virology; Official Journal of the Virology Division of the International Union of Microbiological Societies, Springer-Verlag, VI, vol. 148, No. 3, Jan. 1, 2003, pp. 469-486.
Gerhard W et al: "Prospects for universal influenza virus vaccine", Emerging Infectious Diseases, EID, Atlanta, GA, US, vol. 12, No. 4, Apr. 1, 2006, pp. 569-574.
Chun et al: "Universal antibodies and their applications to the quantitative determination of virtually all subtypes of the influenza A viral hemagglutinins", Elsevier, Vaccine 26, Sep. 3, 2008, pp. 6068-6076.

* cited by examiner

*Primary Examiner* — Bao Li
(74) *Attorney, Agent, or Firm* — Michael R. Williams; Ade & Company Inc.

(57) ABSTRACT

The present invention discloses isolated peptides encoding an antigen or fragments thereof from the N-terminus of hemagglutinin protein of influenza, methods for isolating such antigens and specific uses thereof. The peptide can be used as a vaccine to generate an antibody response that neutralizes influenza infectivity against a variety of influenza strains.

6 Claims, 2 Drawing Sheets

SEQUENCE LISTING

<160> NUMBER OF SEQ ID NOS: 6

<210> SEQ ID NO 1
<211> LENGTH: 14
<212> TYPE: PRT
<213> ORGANISM: Artificial Sequence
<220> FEATURE:
<223> OTHER INFORMATION: synthetic peptide derived from hemagglutinin of
      influenza virus

<400> SEQUENCE: 1

Gly Leu Phe Gly Ala Ile Ala Gly Phe Ile Glu Gly Gly Trp
1               5                   10

<210> SEQ ID NO 2
<211> LENGTH: 14
<212> TYPE: PRT

```
<213> ORGANISM: Artificial Sequence
<220> FEATURE:
<223> OTHER INFORMATION: synthetic peptide derived from hemagglutinin of
      influenza virus

<400> SEQUENCE: 2

Gly Ile Phe Gly Ala Ile Ala Gly Phe Ile Glu Gly Gly Trp
1               5                   10

<210> SEQ ID NO 3
<211> LENGTH: 14
<212> TYPE: PRT
<213> ORGANISM: Artificial Sequence
<220> FEATURE:
<223> OTHER INFORMATION: synthetic peptide derived from hemagglutinin of
      influenza virus

<400> SEQUENCE: 3

Gly Leu Phe Gly Ala Ile Ala Gly Phe Ile Glu Asn Gly Trp
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic peptide derived from hemagglutinin of
      influenza virus

<400> SEQUENCE: 4

Gly Ile Phe Gly Ala Ile Ala Gly Phe Ile Glu Asn Gly Trp
1               5                   10

<210> SEQ ID NO 5
<211> LENGTH: 13
<212> TYPE: PRT
<213> ORGANISM: Artificial Sequence
<220> FEATURE:
<223> OTHER INFORMATION: synthetic peptide derived from hemagglutinin of
      influenza virus

<400> SEQUENCE: 5

Val Thr Gly Leu Arg Asn Ile Pro Ser Ile Gln Ser Arg
1               5                   10

<210> SEQ ID NO 6
<211> LENGTH: 14
<212> TYPE: PRT
<213> ORGANISM: Artificial Sequence
<220> FEATURE:
<223> OTHER INFORMATION: synthetic peptide derived from hemagglutinin of
      influenza virus
<220> FEATURE:
<221> NAME/KEY: VARIANT
<222> LOCATION: (2)..(2)
<223> OTHER INFORMATION: L or I
<220> FEATURE:
<221> NAME/KEY: VARIANT
<222> LOCATION: (12)..(12)
<223> OTHER INFORMATION: G or N

<400> SEQUENCE: 6

Gly Xaa Phe Gly Ala Ile Ala Gly Phe Ile Glu Xaa Gly Trp
1               5                   10
```

INFLUENZA VACCINE

PRIOR APPLICATION INFORMATION

The instant application is a 371 of PCT Application CA10/00623, filed Apr. 29, 2010, now abandoned, which claims the benefit of U.S. Provisional Patent Application, filed Apr. 29, 2009 No. 61/173,842, entitled 'Universal vaccine against influenza virus infection', now abandoned, the contents of which are incorporated herein by reference.

FIELD OF THE INVENTION

The present invention relates to compositions and methods for preventing and treating influenza infections by targeting a conserved area of hemagglutinin and generating an immune response, in particular, a neutralizing antibody response to hemagglutinins.

BACKGROUND OF THE INVENTION

Influenza can infect as much as 5-15% of the world population, resulting in 3-5 million cases of severe illness and up to 500,000 deaths per year. In the US alone, flu epidemics lead to approximately 300,000 influenza-related hospital admissions and 36,000 influenza related deaths annually in addition to an estimated cost of $12 billion per year (Poland 2001; Simonsen et al, 2007, PMID 17897608). Current seasonal influenza vaccines are produced with strains recommended by the World Health Organization about 9-12 months ahead of the targeted season (Carrat et al, 2007). The vaccines typically contain two type A influenza strains and one type B influenza strain, which are predicted to be the most likely strains to cause the upcoming flu epidemic.

However, there are inherent disadvantages associated with the preparation of conventional influenza vaccines such as the uncertainty of the actual circulating strain, the need for annual updating of the manufacturing process and preparation of reagents for vaccine lot release. Furthermore, mismatches between the strains selected for vaccine preparation and the circulating viruses were found to be responsible for much reduced efficacy of the seasonal influenza vaccines (Bridges et al. 2000; De Filette et al. 2005). Clearly, the drawbacks associated with traditional vaccine preparation would be drastically exacerbated in the event of an outbreak of pandemic influenza, given a perceivably much shortened timeframe available for the production of prophylactic vaccines for global needs. All these problems concerning the influenza vaccines are largely due to one single biological property of the influenza virus itself, i.e. the constant mutations of the virus surface proteins hemagglutinin (HA) and neuraminidase (NA). Currently HA is used as the "marker" being tested for vaccine potency (Wood et al. 1999).

Currently, influenza A viruses representing 16 HA and 9 NA subtypes have been detected in wild birds and poultry throughout the world (Zambon 1999; Treanor 2004; Fouchier 2005). Frequent antigenic drifting or shifting of HA and NA prompted numerous exploratory investigations of vaccines that are intended to induce host immune responses against viral proteins that are less subjected to antigenic fluctuations. Of these conserved antigenic determinants, the nucleoproteins (NP) and Matrix (M) have been shown to induce protective immunity against diverse strains of the viruses (Frace et al. 1999; Epstein et al. 2002; de Filette 2005; Mozdzanowska et al. 2003; Fan et al. 2004). Furthermore, it was suggested that cell-mediated immune response rather than humeral immune responses protect the animals immunized with NP-based vaccines while antibody-mediated protections against lethal challenges of various subtypes of influenza virus were reported with the use of M2-based vaccines (Neirynck et al. 1999; de Filette et al 2005; Mozdzanowska et al. 2003). None of these universal vaccines appears to prevent viral infection in animal studies although prevention of clinical diseases was found to be promising (Gerhard et al. 2006).

Given the importance of neutralizing antibodies against HA in preventing influenza infection, the conserved regions in the HA proteins have also received great attention in recent years. The HA1/HA2-joint region has been found to be the most broadly conserved, with the HA2 N-terminal 11 amino acids being conserved among all influenza A subtypes (Horvath et al. 1998; Bianchi et al. 2005; Gerhard et al. 2005). Several groups have reported generation of antibodies against the HA1/HA2 joint region with the use of branched peptides or peptide-carrier conjugate (Nestorowicz et al. 1985; Schoofs 1988; Horvath et al. 1998; Bianchi et al. 2005). Yet, attempts to generate antibodies against the even more universally conserved N-terminus of the HA2 (the fusion peptide) have not been that successful (Jackson, et al. 1991; Nestorowicz et al. 1985; Schoofs 1988; Horvath et al. 1998; Bianchi et al. 2005).

There remains a need in the art for therapies and prevention strategies that can be used to prevent a wide range of infection by various influenza strains.

SUMMARY OF THE INVENTION

According to a first aspect of the invention, there is provided a method of immunizing a host with a peptide sequence from the N-terminus of influenza hemagglutinin and raising an immune response that recognizes the hemagglutinin protein of a variety of influenza subtypes which will cause neutralization of the influenza infection.

According to a second aspect of the invention, there is provided a means of producing a vaccine for influenza by targeting the conserved N-terminus region of hemagglutinin from influenza strains According to a third aspect of the invention, there is provided a means of generating compounds that can inhibit influenza replication that bind to or interact with the conserved region of HA identified.

According to a fourth aspect of the invention, there is provided a means of generating therapeutic compounds for treatment of active influenza infections by screening for binding to the conserved region of HA.

According to an aspect of the invention, there is provided a purified or isolated peptide having the amino acid sequence as set forth in SEQ ID No. 6.

According to a further aspect of the invention, there is provided a method of immunizing an individual against influenza virus comprising administering to said individual an effective amount of a peptide having the amino acid sequence as set forth in SEQ ID No. 6.

According to another aspect of the invention, there is provided a method of preparing a medicament for immunizing an individual against influenza virus comprising admixing a peptide having the amino acid sequence as set forth in SEQ ID No. 6 with a pharmaceutically acceptable excipient, adjuvant or diluent.

DESCRIPTION OF THE PREFERRED EMBODIMENTS

Figure 1:
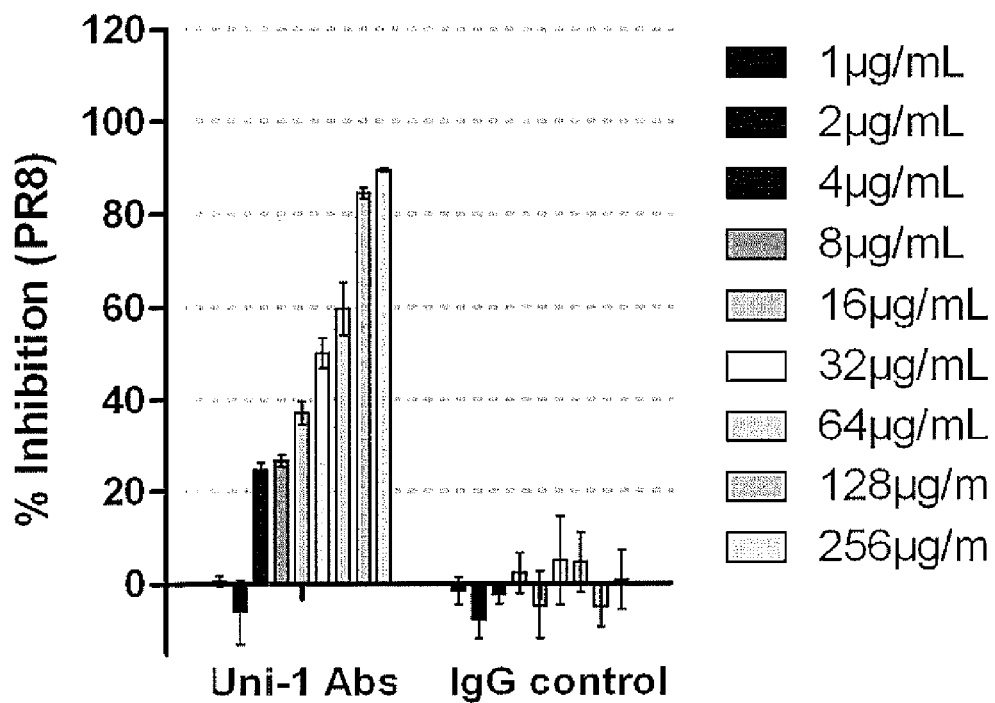
FIG. 1: Inhibition of influenza replication by antibodies generated by vaccination of rabbits with a peptide derived from the N-terminus of HA2 (SEQ ID NO. 1). The virus was pre-incubated with affinity purified antibodies for 30 min at room temperature before they were used to infect MDCK cells. The data show that the Uni-1 antibodies inhibit the virus replication in a dose-response fashion while the negative control (normal rabbit antisera) shows no inhibition of virus replication.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

The present invention is based in part, on the surprising discovery that antibodies to a conserved region of hemagglutinin disable the activity of the hemagglutinin and prevent influenza viral replication.

The practice of the present invention will employ, unless otherwise indicated, conventional methods of chemistry, biochemistry, recombinant DNA techniques and immunology, within the skill of the art. Such techniques are explained fully in the literature. See, e.g., Fundamental Virology, 2nd Edition, vol. I & II (B. N. Fields and D. M. Knipe, eds.); Handbook of Experimental Immunology, Vols. I-IV (D. M. Weir and C. C. Blackwell eds., Blackwell Scientific Publications); T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

Alanine: Ala (A) Arginine: Arg (R) Asparagine: Asn (N) Aspartic acid: Asp (D) Cysteine: Cys (C) Glutamine: Gln (Q) Glutamic acid: Glu (E) Glycine: Gly (G) Histidine: His (H) Isoleucine: Ile (I) Leucine: Leu (L) Lysine: Lys (K) Methionine: Met (M) Phenylalanine: Phe (F) Proline: Pro (P) Serine: Ser (S) Threonine: Thr (T) Tryptophan: Trp (W) Tyrosine: Tyr (Y) Valine: Val (V)

DEFINITIONS

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

By "antigen" is meant a molecule, which contains one or more epitopes that will stimulate a host's immune system to make a cellular antigen-specific immune response when the antigen is presented, or a humoral antibody response. The term "antigen" as used herein denotes both subunit antigens, i.e., proteins which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses a therapeutic or immunogenic protein, or antigenic determinant in vivo, such as in gene therapy and nucleic acid immunization applications, is also included in the definition of antigen herein. Further, for purposes of the present invention, antigens can be derived from any of several known viruses, bacteria, parasites and fungi, as well as any of the various tumor antigens.

An "immunological response" to a selected antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., J. Immunol. (1993) 151:4189-4199; Doe et al., Eur. J. Immunol. (1994) 24:2369-2376.

The terms "effective amount" or "pharmaceutically effective amount" of an adjuvant composition and antigen, as provided herein, refer to a nontoxic but sufficient amount of the composition to provide the desired response, such as an immunological response, and optionally, a corresponding therapeutic effect, or in the case of delivery of a therapeutic protein, an amount sufficient to effect treatment of the subject, as defined below. As will be pointed out below, the exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

The "antigen delivery system" comprises the adjuvant composition, and antigen and other buffers and substances which may be used to stabilize or act as carriers for the combination.

DESCRIPTION OF THE PREFERRED EMBODIMENTS

In the first embodiment, the peptide sequence G(L/I)FGAIAGFIE(G/N)GW (SEQ ID No. 6) is attached to linker and a suitable protein carrier and used as an antigen for influenza vaccinations.

In another embodiment of the invention, the peptide is selected from the group consisting of: GLFGAIAGFIEGGW (SEQ ID NO. 1) (UnM); GIFGAIAGFIEGGW (SEQ ID NO. 2) (Uni-2); GLFGAIAGFIENGW (SEQ ID NO. 3) (Uni-3); and GIFGAIAGFIENGW (SEQ ID NO. 4) (Uni-4).

As discussed herein, administration of an effective amount of a peptide as discussed above will elicit an immune response in an individual. As discussed above, these peptides have the surprising effect of inducing neutralizing immunity, that is, the generation of antibodies which interfere with influenza virus replication.

In one embodiment of the invention, there is provided a purified or isolated peptide having the amino acid sequence as set forth in SEQ ID No. 6. In yet another aspect of the invention, there is provided a purified or isolated peptide having the amino acid sequence as set forth in one of SEQ ID No. 1-4. In a preferred embodiment, the peptide has the amino acid sequence as set forth in SEQ ID No. 1.

In an embodiment of the invention, there is provided the use of a purified or isolated peptide having the amino acid sequence as set forth in SEQ ID No. 6 to immunize an individual in need of such treatment against influenza virus. In yet another aspect of the invention, there is provided a purified or isolated peptide having the amino acid sequence as set forth in one of SEQ ID No. 1-4. In a preferred embodiment, the peptide has the amino acid sequence as set forth in SEQ ID No. 1. As discussed herein, this will induce neutralizing immunity against one or more influenza virus strains.

In a further embodiment of the invention, there is provided a composition comprising a peptide having the amino acid sequence as set forth in SEQ ID No. 6 attached by a suitable linker to a suitable carrier protein. In yet another aspect of the invention, there is provided a peptide having the amino acid sequence as set forth in one of SEQ ID No. 1-4 attached by a suitable linker to a suitable carrier protein. In a preferred embodiment, the peptide has the amino acid sequence as set forth in SEQ ID No. 1. As will be appreciated by one of skill in the art, such a composition may be used to immunize or inoculate an individual desirous of such treatment so as to induce the formation of antibodies against influenza in said individual. As discussed above, the antibodies may be neutralizing antibodies which interfere with influenza viral replication. In the examples, the carrier is Keyhole Limpet Hemocyanin (KLH) although as will be appreciated by one of skill in the art, any suitable carrier known in the art, for example, BSA, tetanis toxid or hepatitis core protein (HBc) may be used in accordance with the invention.

In another embodiment of the invention, there is provided a method of immunizing an individual against influenza virus infection comprising administering to said individual an effective amount of the composition described above. As discussed herein, 'an effective amount' in this context refers to an amount that is sufficient to induce an immune response in said individual against an influenza virus.

In another embodiment of the invention, there is provided a method of preparing a medicament for immunizing an individual against influenza virus infection comprising admixing a peptide having the amino acid sequence as set forth in SEQ ID No. 6 with a pharmaceutically acceptable excipient, adjuvant or diluent. Specifically, the pharmaceutically acceptable excipient, adjuvant or diluent is one that is suitable for injection into the individual to be treated, that is, the individual to be immunized against an influenza virus infection. Alternatively, the peptide may have the amino acid sequence as set forth in one of SEQ ID No. 1-4. In a preferred embodiment, the peptide has the amino acid sequence as set forth in SEQ ID No. 1. In some embodiments, the peptide is attached by a suitable linker to a suitable carrier protein.

In yet another embodiment, the subject invention is directed to a method of generating one or more therapeutic compounds useful for treating an active influenza infection.

EXAMPLES

Below are examples of specific embodiments for carrying out the present invention. The examples are offered for illustrative purposes only, and are not intended to limit the scope of the present invention in any way.

Example 1

All (12,451) HA Inf A protein sequences from, avian, human, and swine hosts full sequences, including 2009 pandemic sequences were downloaded from the NCBI flu resource database on Apr. 13, 2010. The sequences were then filtered such that only sequences representing a unique combination of host, location, subtype, and collection year were selected in order to reduce overrepresentation of strains collected in a given region at a given time. This reduces the set to 1905 sequences. Sequences containing ambiguity codes (BJOUXZ) were removed from the set, reducing the total to 1843. Unusually short sequences were also removed from the set, giving a final number of 1068 sequences for analysis. Sequences were multiply aligned using clustalw-mpi.

Figure 3:
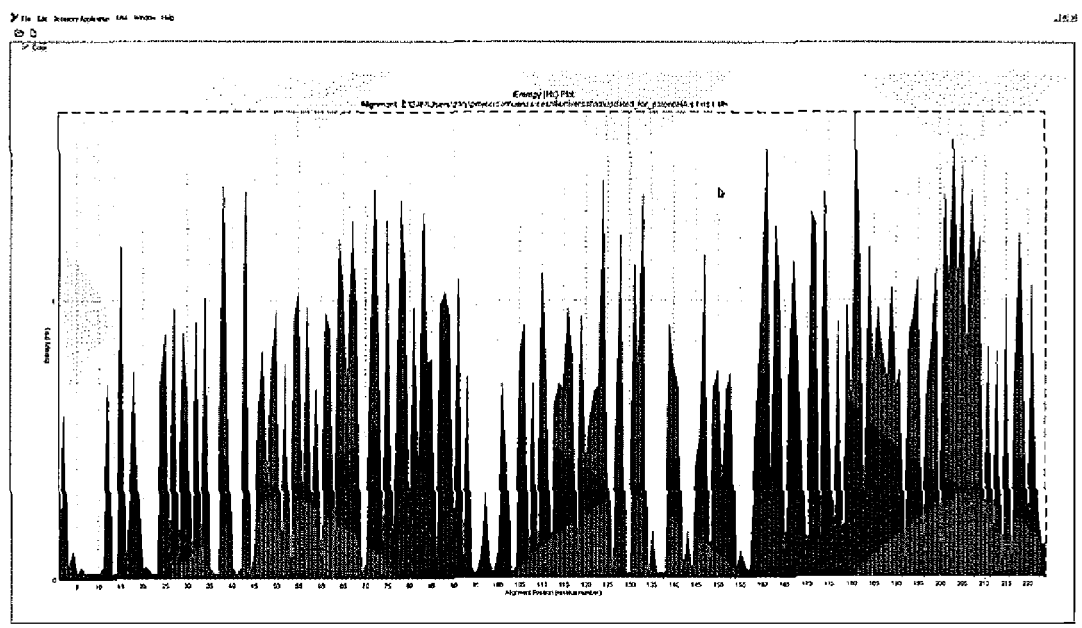
FIG. 3: Shannon Entropy plot. The aligned sequences of 1068 HA sequences from HA showing the Shannon Entropy. Lower values indicate a more conserved sequence. The shaded area indicates the identified neutralizing antigen region.

The sequences from ncbi are the immature polyprotein sequences; this poly protein is cleaved when mature into two ha sequences: ha1 and ha2. The fusion peptide resides at the N-terminus of HA2, the alignment was then edited such that the alignment only contains the HA2 region, with the fusion peptide residing at position 1 of the alignment (because the mature peptide begins at this position, it doesnt make sense to examine the upstream variability from the polyprotein). The Shannon entropy was calculated at each position of the alignment, and plotted the value out as an entropy plot. The lower the value, the more conserved. The shaded region in FIG. 3 shows the antigen sequence. Four peptides were selected to ensure a good coverage of the fusion peptide region. These peptides, GLFGAIAGFIEGGW (SEQ ID NO: 1) (UnM); GIFGAIAGFIEGGW (SEQ ID NO: 2) (Uni-2); GLFGAIAGFIENGW (SEQ ID NO: 3) (Uni-3); and GIFGAIAGFIENGW (SEQ ID NO: 4) (Uni-4).

TABLE 1

Amino acid variation of the N-terminus of HA based on comparison of 1068 strains of influenza

| Position | AA | # | AA | # | AA | # | AA | # | AA | # |
|---|---|---|---|---|---|---|---|---|---|---|
| 1 | G | 1068 | | | | | | | | |
| 2 | L | 873 | I | 194 | F | 1 | | | | |
| 3 | F | 1067 | L | 1 | | | | | | |
| 4 | G | 1062 | S | 2 | E | 2 | D | 1 | V | 1 |
| 5 | A | 1067 | Q | 1 | | | | | | |
| 6 | I | 1066 | K | 1 | L | 1 | | | | |
| 7 | A | 1066 | L | 1 | V | 1 | | | | |
| 8 | G | 1067 | D | 1 | | | | | | |
| 9 | F | 1068 | | | | | | | | |
| 10 | I | 1067 | F | 1 | | | | | | |
| 11 | E | 1067 | Q | 1 | | | | | | |
| 12 | G | 735 | N | 332 | E | 1 | | | | |
| 13 | G | 1068 | | | | | | | | |
| 14 | W | 1068 | | | | | | | | |

This table shows amino acid variability in the N-terminus of HA. For example, at position 1, all 1068 strains analyzed had a glycine residue; however, at position 2, 873 strains had a leucine residue while 194 strains had an isoleucine residue and one strain had a phenylalanine residue.

Example 2

Preparation of Peptides and their Conjugates for Immunization

Bioinformatics approach was employed to locate the presence of the universally conserved region in the HAs. Sequences from public domains (the NCBI flu resource) were retrieved separately for each subtype. The combined human and avian influenza HA sequences with identical sequences were removed. Next, a separate multiple alignment for each subtype was performed, followed by the extraction of the target region from the full-gene alignment. The Shannon entropy for each position of amino acid of the identified consensus sequences was then calculated to determine the degree of variation. Four peptides were selected to ensure a good coverage of the fusion peptide region. These peptides, GLFGAIAGFIEGGW (SEQ ID NO: 1) (UnM); GIFGAIAG-FIEGGW (SEQ ID NO: 2) (Uni-2); GLFGAIAGFIENGW (SEQ ID NO: 3) (Uni-3); and GIFGAIAGFIENGW (SEQ ID NO: 4) (Uni-4), were then modified and conjugated in a procedure described previously with minor modification (Wu et al. 1993; Das Sarma et al. 2005). In brief, the peptides were first linked to 6-aminocaproic acid, followed by an addition of a tripeptide (KKC). The modified peptides were then conjugated to the carrier protein KLH using sulfosuccinimidyl-4-(N-maleimidomethyl)cyclohexane-1-carboxylate (Sulfo-SMCC) as cross-linking reagent and purified according to the manufacturer's instruction manual (Fisher Canada, Nepean, On.). Table 1 summarizes the peptides (Uni-1, Uni-2, Uni-3 and Uni-4) and conjugates thereof used for the generation and characterization of specific antibodies against the N-terminus of influenza viruses.

Table 1 depicts the four peptides (Uni-1 to Uni-4) located at the N-terminus of HA2 of influenza virus strains. The selection of these peptides was based on bioinformatics analyses of all available influenza HA sequences and represent the most conserved amino acid sequences in the fusion peptide region with minor variations. HA1-C is a control peptide VTGLR-NIPSIQSR (SEQ ID NO: 5) located at the C-terminus of HA1. Acp denotes 6-aminocaproic acid, an effective spacer to link haptens (dinitrophenyl) to carrier proteins (Scott et al. 1984). KKC represent a tripeptide, which was used here to facilitate solubilization of the carrier-free peptides in aqueous solution for antigen-antibody interaction in ELISA. KLH designates keyhole limpet hemocyanin.

TABLE 2

Sequences of peptides used:

| SEQ ID NO | Peptide sequence | Alternative identification |
|---|---|---|
| 1 | GLFGAIAGFIEGGW | Uni-1 |
| 2 | GIFGAIAGFIEGGW | Uni-2 |
| 3 | GLFGAIAGFIENGW | Uni-3 |
| 4 | GIFGAIAGFIENGW | Uni-4 |
| 5 | VTGLRNIPSIQSR | Control peptide |

Example 3

Generation of Vaccine by Immunizing with Peptide

Rabbits and sheep were immunized with peptide of sequence GLFGAIAGFIEGGW (SEQ ID No. 1) conjugated to 6-aminocaproic acid spacer, and a tripeptide (KKC) and a protein carrier (KLH) according to standard techniques and antibodies isolated by affinity chromatography. Antibodies that recognized a number of influenza strains were identified. These antibodies bound to hemagluttinins from multiple strains of influenza as shown in western blots.

Production of Antibodies Against the Fusion Peptides of HAs

NZW rabbits were obtained from Jackson Laboratory. All animal experiments were conducted in accordance with the Institutional Guidelines and Protocols for Animal Experiments. The animals were immunized subcutaneously with peptide of sequence GLFGAIAGFIEGGW (SEQ ID No. 1) conjugated to 6-aminocaproic acid spacer, and a tripeptide (KKC) and a protein carrier (KLH) mixed with freund complete adjuvant (FCA) at 200 μg per injection, and boosted every three weeks with the same doses of antigen in Freund incomplete adjuvant. The antibodies were purified by using the peptides as ligands in affinity columns in a procedure described previously (Wu et al. 1993). In brief, the antisera were incubated with 5 mL of the peptide on a column for 10 min at room temperature, followed by washing the column at least 5 times with PBS and 0.1% Tween™-20. The antibodies were then eluted with acetate buffer (pH 2.0), followed by immediate addition of sodium hydroxide to bring the pH to 7.2 (Wu et al., 1993).

Immunoblotting

The specificities of the antibodies were determined in Western Blot using a procedure with minor modifications as described (Casley et al. 2007). In brief, allantoic fluids directly from eggs inoculated with viruses were fractionated on sodium dodecyl sulfate (SDS)-10% polyacrylamide gel, followed by transferring the samples to a nitrocellulose filter. The nitrocellulose filter was then blocked with 5% BSA/PBS at 37° C. for 1 hr. Following incubation of filters for 1 hr at 37° C. with rabbit antisera against HA peptides as described above, peroxidase-conjugated goat anti-rabbit immunoglobulin (Ig) G (Sigma, Oakville, Canada) was added for an additional incubation of 1 h at room temperature, followed by chemiluminescent detection (ECL, Amersham Pharmacia Biotech, Piscataway, N.J.). In some cases, dot blotting was used to determine antigen-antibody interaction. The procedure is essentially the same as Western Blot except that the antigens (10 μl) were directly spotted on the nitrocellulose filter.

ELISA

Indirect ELISA was performed in a procedure as described (Huang et al 2008). In brief, 4 μg/mL of HA protein or 1 μg/mL of peptides were coated onto 96-well plate (Nunc/VWR, Mississauga, ON) at 4° C. overnight. The wells were then washed five times with PBS, 0.05% Tween™-20, followed by the addition of blocking buffer comprised of PBS, 0.05% Tween™-20 and 5% BSA. After incubation at 37° C. for 1 h, the blocking buffer was removed, followed by the addition of primary antibodies. The plates were incubated again at 37° C. for 1 h. Afterwards, secondary antibodies (peroxidase-conjugated goat anti-rabbit IgG, IgM or IgA) were added at concentrations recommended by the supplier (Cedarlane Labs). Following an additional incubation at 37° C. for 1 h, the plates were washed five times before o-phenylenediamine dihydrochloride (OPD) was added for colorimetric development. The cut-off was defined as mean of five negative samples (from pre-bleed control) plus two STD.

Competitive ELISA was performed as described below. The antigens were first denatured with 8 M in PBS urea for 20 min at room temperature, followed by mixing with equal volume of PBS to allow final concentration of antigen at 4 μg/mL in 4 M urea/PBS.

The antigens were then used to coat the Nunc 96-well plate at 4° C. overnight. The next day, the antigens were denatured with 8 M urea/PBS for 20 min at room temperature, followed by mixing with 8,000× diluted antisera. The final concentration of urea in the antigen-antibody mixture is 4 M. The mixture was then transferred to the aforementioned 96-well ELISA plate which had been pre-coated with the antigens and subsequently blocked with 5% BSA/PBS. The plate was then incubated at 37° C. for 1 hr. The rest of the procedure was the same as that in ELISA.

Example 4

Inhibition of Viral Replication by Antibody

Antibodies from rabbits immunized with peptides were purified by affinity chromatography and increasing concentrations were added to cultures that were infected with influenza strain A/Puerto Rico/8/34 (H1N1). The data show that there is a dose response curve, with higher amounts of antibody preventing the replication of the influenza virus, as shown in FIG. 1.

Example 5

Figure 2:
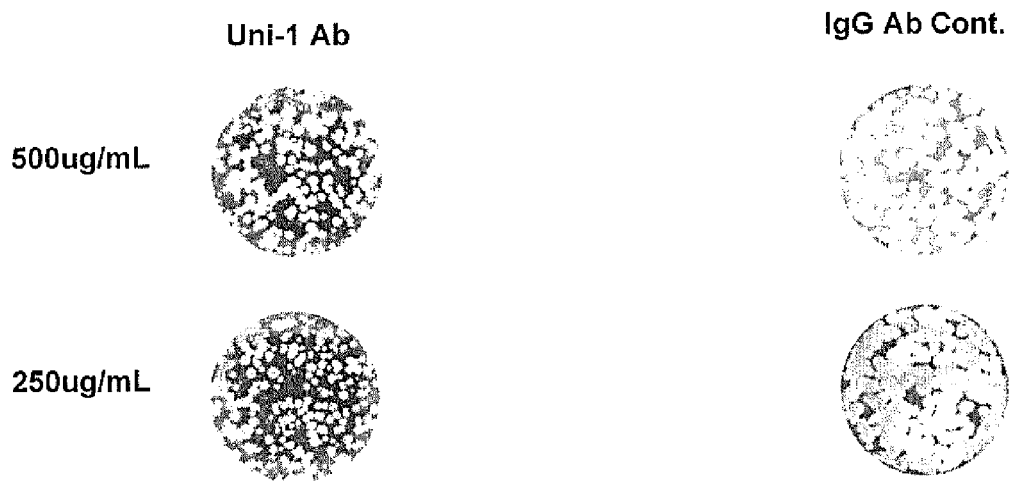
FIG. 2: Antibodies that recognize the peptide derived from the N-terminus of HA2 (SEQ ID NO. 1) cause a reduction in plaque formation in culture. The virus was pre-incubated with affinity purified antibodies for 30 min at room temperature before they were used to infect MDCK cells. The infectivity of the virus treated as such was then analyzed by plaque assay in a procedure as described (Hashem A et al, 2009). The data show that the antibody reduced the size of the plaque, showing that the antibodies can inhibit virus replication

Antibodies that Recognize SEQ ID NO 1 Cause a Reduction in Plaque Formation in Culture Rabbits were immunized with the peptide of SEQ ID NO 1 conjugated to KLH and antibodies isolated according to standard practices as described in Example 2. The virus was pre-incubated with affinity purified antibodies for 30 min at room temperature before they were used to infect MDCK cells. The infectivity of the virus treated as such was then analyzed by plaque assay in a procedure as described (Hashem A et al, 2009). The data show that the antibody reduced the size of the plaque, showing that the antibodies can inhibit virus replication. Higher concentrations of antibody led to smaller plaques demonstrating that viral replication was being inhibited, as shown in FIG. 2.

Example 6

As can be seen, the peptides encoded by SEQ IDs NO 1-4 are therapeutic targets. Accordingly, this information can be used to generate compounds that could be used to bind/interfere with activity of hemagglutinin. As will be appreciated by one of skill in the art, such compounds include but are by no means limited to: antisense compounds, DNA, RNA, proteins, peptides, small molecules, sugars and the like. In addition, antibodies to the peptide could be used to screen a variety of compounds. Furthermore, the peptides could be used to bind to mimotopes which would then be screened for example in a plaque test to determine if there was inhibition of influenza activity. A variety of influenza strains will be tested in this manner.

Example 7

Generation of a Therapeutic Drug

As will be appreciated by one of skill in the art, the peptides of any one of SEQ IDs NO 1-4 can be used to screen for drugs/compounds that bind to these peptides. These drugs/compounds will then be screened using traditional drug screening technologies to identify compounds that are both safe, effective and can be generated in commercially useful quantities. As will be appreciated by one of skill in the art, these drugs may be scFv, antibodies, DNA, RNA, proteins, small molecules, lipids, or the like. It is also of note that these could also be generated in silico.

While the preferred embodiments of the invention have been described above, it will be recognized and understood that various modifications may be made therein, and the appended claims are intended to cover all such modifications which may fall within the spirit and scope of the invention.

REFERENCES

Bianchi E, et al. Universal influenza B vaccine based on the maturational cleavage site of the hemagglutinin precursor. J Virol. (2005 June); 79(12):7380-8.

Bridges C B, et al. Effectiveness and cost-benefit of influenza vaccination of healthy working adults: A randomized controlled trial. JAMA. (2000 Oct. 4); 284(13): 1655-63.

Carrat F and Flahault A. Influenza vaccine: the challenge of antigenic drift. Vaccine. (2007 Sep. 28); 25(39-40):6852-62.

Das Sarma J, et al. Antibody to folic acid: increased specificity and sensitivity in ELISA by using epsilon-aminocaproic acid modified BSA as the carrier protein. J Immunol Methods. (1995 Jul. 17); 184(1):1-6.

De Filette M, et al. Universal influenza A vaccine: optimization of M2-based constructs. Virology. (2005 Jun. 20); 337(1): 149-61.

Epstein S L, et al. DNA vaccine expressing conserved influenza virus proteins protective against H5N1 challenge infection in mice. Emerg Infect Dis. (2002 August); 8(8): 796-801.

Findlay J W and Dillard R F. Appropriate calibration curve fitting in ligand binding assays. AAPS J. (2007 Jun. 29); 9(2):E260-7.

Fouchier R A, et al. Characterization of a novel influenza A virus hemagglutinin subtype (H16) obtained from black-headed gulls. J. Virol. (2005 March); 79(5):2814-22.

Frace A M, et al. Modified M2 proteins produce heterotypic immunity against influenza A virus. Vaccine. (1999 May 4); 17(18):2237-44.

Fan J, Liang X, et al. Preclinical study of influenza virus A M2 peptide conjugate vaccines in mice, ferrets, and rhesus monkeys. Vaccine. (2004 Aug. 13); 22(23-24):2993-3003.

Gerhard W, et al. Prospects for universal influenza virus vaccine. Emerg Infect Dis. (2006 April); 12(4):569-74.

Gerhard W. Induction of influenza type A virus-specific resistance by immunization of mice with a synthetic multiple antigenic peptide vaccine that contains ectodomains of matrix protein 2. Vaccine. (2003 Jun. 2); 21 (19-20)2616-26.

Horvath A, et al. A hemagglutinin-based multipeptide construct elicits enhanced protective immune response in mice against influenza A virus infection. Immunol Lett. (1998 February); 60(2-3): 127-36.

Jackson D C and Brown L E. A synthetic peptide of influenza virus hemagglutinin as a model antigen and immunogen. Pept Res. (1991 May-June); 4(3):114-24.

Jackson D C, et al. The central role played by peptides in the immune response and the design of peptide-based vaccines against infectious diseases and cancer. Curr Drug Targets. (2002 April); 3(2): 175-96.

Neirynck S, et al. A universal influenza A vaccine based on the extracellular domain of the M2 protein. Nat Med. (1999 October); 5(10): 1157-63.

Nestorowicz A, et al. Antibodies elicited by influenza virus hemagglutinin fail to bind to synthetic peptides representing putative antigenic sites. Mol Immunol. (1985 February); 22(2): 145-54.

Poland G A, et al. Influenza vaccines: a review and rationale for use in developed and underdeveloped countries. Vaccine. (2001 Mar. 21); 19(17-19):2216-20.

Rohm C, et al. Characterization of a novel influenza hemagglutinin, H15: criteria for determination of influenza A subtypes. Virology. (1996 Mar. 15); 217(2):508-16.

Schoofs P G, et al. Epitopes of an influenza viral peptide recognized by antibody at single amino acid resolution. J Immunol. (1988 Jan. 15); 140(2):611-6.

Scott D, et al. Immunogenicity of biotinylated hapten-avidin complexes. Mol Immunol. (1984 November); 21 (11):1055-60.

Simonsen L, et al. Mortality benefits of influenza vaccination in elderly people: an ongoing controversy. Lancet Infect Dis. (2007 October); 7(10):658-66.

Treanor J. Influenza vaccine-outmaneuvering antigenic shift and drift. N Engl J. Med. (2004 Jan. 15); 350(3):218-20.

Tomasini B R and Mosher D F. Conformational states of vitronectin: preferential expression of an antigenic epitope when vitronectin is covalently and noncovalently complexed with thrombin-antithrombin III or treated with urea. Blood. (1988 September); 72(3):903-12.

Wang K, et al. Expression and purification of an influenza hemagglutinin—one step closer to a recombinant protein-based influenza vaccine. Vaccine. (2006 Mar. 15); 24(12): 2176-85.

World Health Organization. (1980). A revision of the system of nomenclature for influenza viruses: a W.H.O. memorandum. Bull. W. H. O 58:585-591.

Wood J M, et al. The influence of the host cell on standardisation of influenza vaccine potency. Dev Biol Stand. (1999); 98:183-8; discussion 197.

Wu J, et al. Monoclonal antibody-mediated inhibition of HIV-1 reverse transcriptase polymerase activity. Interaction with a possible deoxynucleoside triphosphate binding domain. J Biol Chem. (1993 May 15); 268(14):9980-5.

Zambon M C. Epidemiology and pathogenesis of influenza. J Antimicrob Chemother. (1999 November); 44 Suppl B:3-9.

WO 2009/111865

The invention claimed is:

1. A method of immunizing an individual against influenza virus comprising inducing a neutralizing immunity against influenza virus in said individual by administering to said individual an effective amount of a conjugate comprising a peptide consisting of the amino acid sequence as set forth in SEQ ID No. 6 connected by a linker to a carrier protein such that antibodies that interfere with an influenza virus replication are generated.

2. The method according to claim 1 wherein the peptide is selected from the group consisting of: GLFGAIAGFIEGGW (SEQ ID NO. 1); GIFGAIAGFIEGGW (SEQ ID NO. 2); GLFGAIAGFIENGW (SEQ ID NO. 3); and GIFGAIAGFIENGW (SEQ ID NO. 4).

3. The method according to claim 1 wherein the linker comprises 6-aminocaproic acid.

4. The method according to claim 1 wherein the linker further comprises KKC.

5. The method according to claim 1 wherein the carrier protein is selected from the group consisting of: Keyhole Limpet Hemocyanin; Bovine Serum Albumin; tetanis toxoid; and Hepatitis core protein.

6. The method according to claim 1 wherein the carrier protein is Keyhole Limpet Hemocyanin.

* * * * *